United States Patent
Dubson et al.

(10) Patent No.: US 7,244,116 B2
(45) Date of Patent: Jul. 17, 2007

(54) APPARATUS FOR IMPROVING MECHANICAL CHARACTERISTICS OF NONWOVEN MATERIALS

(75) Inventors: Alexander Dubson, Hadera (IL); Eli Bar, Moshav Megadim (IL)

(73) Assignee: Nicast Ltd., Lod (IL)

( * ) Notice: Subject to any disclaimer, the term of this patent is extended or adjusted under 35 U.S.C. 154(b) by 583 days.

(21) Appl. No.: 10/471,277

(22) PCT Filed: Mar. 19, 2002

(86) PCT No.: PCT/IL02/00218

§ 371 (c)(1),
(2), (4) Date: Sep. 17, 2003

(87) PCT Pub. No.: WO02/074189

PCT Pub. Date: Sep. 26, 2002

(65) Prior Publication Data

US 2004/0096533 A1    May 20, 2004

Related U.S. Application Data

(60) Provisional application No. 60/276,956, filed on Mar. 20, 2001, provisional application No. 60/256,323, filed on Dec. 19, 2000.

(51) Int. Cl.
*B29B 13/02* (2006.01)

(52) U.S. Cl. .................. 425/174.8 R; 425/174.8 E

(58) Field of Classification Search ......... 425/174.8 E, 425/174.8 R
See application file for complete search history.

(56) References Cited

U.S. PATENT DOCUMENTS 2,491,889 A    12/1949  Bennett et al.

(Continued)

FOREIGN PATENT DOCUMENTS

EP          0223374        5/1987

(Continued)

*Primary Examiner*—Yogendra N. Gupta
*Assistant Examiner*—Maria Veronica Ewald

(57) ABSTRACT

An apparatus for forming a nonwoven material from a liquefied polymer, the apparatus comprising: (a) a precipitation electrode; (b) a dispenser spaced apart from the precipitation electrode, and defining a first axis therebetween, the dispenser being at a first potential relative to the precipitation electrode; and (c) a system of electrodes being laterally displaced from the dispenser, being at a second potential relative to the precipitation electrode and capable of providing an electric field having at least one rotating component about the first axis; the dispenser and the system of electrodes being designed and constructed such that the liquefied polymer is dispensed from the dispenser and forms a plurality of entangled fibers moving in a direction of the precipitation electrode, hence forming the nonwoven material thereupon.

16 Claims, 4 Drawing Sheets

U.S. PATENT DOCUMENTS

| | | | |
|---|---|---|---|
| 3,280,229 | A | 10/1966 | Simons |
| 3,425,418 | A | 2/1969 | Chvapil et al. |
| 3,625,745 | A | 12/1971 | Wright et al. |
| 3,688,317 | A | 9/1972 | Kurtz |
| 3,860,369 | A * | 1/1975 | Brethauer et al. ............. 425/3 |
| 4,044,404 | A | 8/1977 | Martin et al. |
| 4,159,640 | A | 7/1979 | Lévèque et al. |
| 4,223,101 | A | 9/1980 | Fine et al. |
| 4,323,525 | A | 4/1982 | Bornat |
| 4,345,414 | A * | 8/1982 | Bornat et al. ................. 53/425 |
| 4,368,277 | A | 1/1983 | Burinsky et al. |
| 4,475,972 | A | 10/1984 | Wong |
| 4,524,036 | A | 6/1985 | Gilding et al. |
| 4,657,793 | A | 4/1987 | Fisher |
| 4,689,186 | A * | 8/1987 | Bornat .......................... 264/6 |
| 4,738,740 | A | 4/1988 | Pinchuk et al. |
| 4,739,013 | A | 4/1988 | Pinchuk |
| 4,743,252 | A | 5/1988 | Martin et al. |
| 4,759,757 | A | 7/1988 | Pinchuk |
| 4,769,030 | A | 9/1988 | Pinchuk |
| 4,798,606 | A | 1/1989 | Pinchuk |
| 4,802,145 | A | 1/1989 | Mount II |
| 4,842,505 | A | 6/1989 | Annis et al. |
| 4,872,455 | A | 10/1989 | Pinchuk et al. |
| 4,878,908 | A | 11/1989 | Martin et al. |
| 4,880,002 | A | 11/1989 | MacGregor |
| 4,904,174 | A | 2/1990 | Moosmayer et al. |
| 4,905,367 | A | 3/1990 | Pinchuk et al. |
| 4,965,110 | A | 10/1990 | Berry |
| 4,990,158 | A | 2/1991 | Kaplan et al. |
| 4,997,600 | A | 3/1991 | Okumura et al. |
| 5,019,090 | A | 5/1991 | Pinchuk |
| 5,024,671 | A | 6/1991 | Tu et al. |
| 5,024,789 | A | 6/1991 | Berry |
| 5,084,065 | A | 1/1992 | Weldon et al. |
| 5,092,877 | A | 3/1992 | Pinchuk |
| 5,116,360 | A | 5/1992 | Pinchuk et al. |
| 5,133,742 | A | 7/1992 | Pinchuk |
| 5,147,725 | A | 9/1992 | Pinchuk |
| 5,226,913 | A | 7/1993 | Pinchuk |
| 5,298,255 | A | 3/1994 | Sawamoto et al. |
| 5,334,201 | A | 8/1994 | Cowan |
| 5,360,397 | A | 11/1994 | Pinchuk |
| 5,376,117 | A | 12/1994 | Pinchuk et al. |
| 5,383,922 | A | 1/1995 | Zipes et al. |
| 5,383,928 | A | 1/1995 | Scott et al. |
| 5,415,664 | A | 5/1995 | Pinchuk |
| 5,419,760 | A | 5/1995 | Narciso |
| 5,545,208 | A | 8/1996 | Wolff et al. |
| 5,549,663 | A | 8/1996 | Cottone |
| 5,554,722 | A | 9/1996 | Eichenauer et al. |
| 5,558,809 | A | 9/1996 | Groh et al. |
| 5,575,818 | A | 11/1996 | Pinchuk |
| 5,591,227 | A | 1/1997 | Dinh et al. |
| 5,609,629 | A | 3/1997 | Fearnot et al. |
| 5,624,411 | A | 4/1997 | Tuch |
| 5,627,368 | A | 5/1997 | Moake |
| 5,628,788 | A | 5/1997 | Pinchuk |
| 5,632,772 | A | 5/1997 | Alcime et al. |
| 5,637,113 | A | 6/1997 | Tartaglia et al. |
| 5,639,278 | A | 6/1997 | Dereume et al. |
| 5,653,747 | A | 8/1997 | Dereume |
| 5,697,967 | A | 12/1997 | Dinh et al. |
| 5,700,269 | A | 12/1997 | Pinchuk et al. |
| 5,723,004 | A | 3/1998 | Dereume et al. |
| 5,725,567 | A | 3/1998 | Wolff et al. |
| 5,726,107 | A | 3/1998 | Dahringer et al. |
| 5,733,327 | A | 3/1998 | Igaki et al. |
| 5,741,333 | A | 4/1998 | Frid |
| 5,749,921 | A | 5/1998 | Lenker et al. |
| 5,755,722 | A | 5/1998 | Barry et al. |
| 5,755,774 | A | 5/1998 | Pinchuk |
| 5,766,710 | A | 6/1998 | Turnlund et al. |
| 5,797,887 | A | 8/1998 | Rosen et al. |
| 5,824,048 | A | 10/1998 | Tuch |
| 5,824,049 | A | 10/1998 | Ragheb et al. |
| 5,837,008 | A | 11/1998 | Berg et al. |
| 5,843,172 | A | 12/1998 | Yan |
| 5,849,037 | A | 12/1998 | Frid |
| 5,855,598 | A | 1/1999 | Pinchuk |
| 5,871,538 | A | 2/1999 | Dereume |
| 5,900,246 | A | 5/1999 | Lambert |
| 5,928,247 | A | 7/1999 | Barry et al. |
| 5,938,697 | A | 8/1999 | Killion et al. |
| 5,948,018 | A | 9/1999 | Dereume et al. |
| 5,968,070 | A | 10/1999 | Bley et al. |
| 5,968,091 | A | 10/1999 | Pinchuk et al. |
| 5,980,551 | A | 11/1999 | Summers et al. |
| 5,980,972 | A | 11/1999 | Ding |
| 6,001,125 | A | 12/1999 | Golds et al. |
| 6,004,346 | A | 12/1999 | Wolff et al. |
| 6,013,099 | A | 1/2000 | Dinh et al. |
| 6,017,362 | A | 1/2000 | Lau et al. |
| 6,019,789 | A | 2/2000 | Dinh et al. |
| 6,023,170 | A | 2/2000 | Hilhorst et al. |
| 6,102,212 | A | 8/2000 | Strid |
| 6,102,939 | A | 8/2000 | Pinchuk |
| 6,106,913 | A | 8/2000 | Scardino et al. |
| 6,117,425 | A | 9/2000 | MacPhee et al. |
| 6,165,212 | A | 12/2000 | Dereume et al. |
| 6,252,129 | B1 | 6/2001 | Coffee |
| 6,265,333 | B1 | 7/2001 | Dzenis et al. |
| 6,270,793 | B1 | 8/2001 | Van Dyke et al. |
| 6,306,424 | B1 | 10/2001 | Vyakarnam et al. |
| 6,308,509 | B1 | 10/2001 | Scardino et al. |
| 6,309,413 | B1 | 10/2001 | Dereume et al. |
| 6,604,925 | B1 | 8/2003 | Dubson |
| 2001/0020652 | A1 | 9/2001 | Kadlubowski et al. |
| 2002/0002395 | A1 | 1/2002 | Berg et al. |
| 2002/0081732 | A1 | 6/2002 | Bowlin et al. |
| 2003/0191519 | A1 | 10/2003 | Lombardi et al. |

FOREIGN PATENT DOCUMENTS

| | | |
|---|---|---|
| EP | 0253539 | 1/1988 |
| GB | 2142870 | 1/1985 |
| WO | 0523960 | 1/1993 |
| WO | WO 01/54667 | 2/2001 |
| WO | WO 01/66035 | 9/2001 |
| WO | WO 02/40242 | 5/2002 |
| WO | WO 02/49535 | 6/2002 |
| WO | WO 02/49536 | 6/2002 |
| WO | WO 02/49678 | 6/2002 |
| WO | WO 02/074190 | 9/2002 |
| WO | WO 02/074191 | 9/2002 |

* cited by examiner

APPARATUS FOR IMPROVING MECHANICAL CHARACTERISTICS OF NONWOVEN MATERIALS

RELATED PATENT APPLICATION

This application is a National Phase Application of PCT/IL02/00218 International Filing Date 19 Mar. 2002, which claims priority from U.S. patent application Ser. No. 09/982.017 filed 19 Oct. 2001, which claims priority from U.S. Provisional Patent Application No. 60/276,956 filed 20 Mar. 2001 and claims priority from U.S. Provisional Patent Applicant No. 60/256,323 filed 19 Dec. 2000.

FIELD AND BACKGROUND OF THE INVENTION

The present invention relates to a method and apparatus for manufacturing a nonwoven material and, more particularly, to a method and apparatus of manufacturing a nonwoven material using electroejection.

Production of fibrous products is described in various patents inter alia using the technique of electrospinning of liquefied polymer, so that products comprising polymer fibers are obtained. Electrospinning is a method for the manufacture of ultra-thin synthetic fibers, which reduces the number of technological operations and increases the stability of properties of the product being manufactured.

The process of electrospinning creates a fine stream or jet of liquid that upon proper evaporation of a solvent or liquid to solid transition state will yield a nonwoven structure. The fine stream of liquid is produced by pulling a small amount of polymer solution through space by using electrical forces. More particularly, the electrospinning process involves the subjection of a liquefied substance, such as polymer, into an electric field, whereby the liquid is caused to produce fibers that are drawn by electric forces to an electrode, and are, in addition, subjected to a hardening procedure. In the case of liquid which is normally solid at room temperature, the hardening procedure may be mere cooling; however other procedures such as chemical hardening (polymerization) or evaporation of solvent may also be employed. The produced fibers are collected on a suitably located precipitation device and subsequently stripped from it. The sedimentation device is typically shaped in accordance with the desired geometry of the final product, which may be for example tubular, flat or even an arbitrarily shaped product.

Examples of tubular fibrous product which can be manufactured via electrospinning are vascular prosthesis, particularly a synthetic blood vessel, and tubes through which a wire or other device or structure may pass or lie. Tubular fibrous products may also be used as various kinds of artificial ducts, such as, for example, urinary, air or bile duct.

Nonwoven materials manufactured via electrospinning may be shaped in a form appropriate for use as a wound dressing. A particular advantage of the use of electrospun materials is that the fibers may be of very small diameter, to give a mat with small interstices and consequently a high surface area.

Additional examples of end uses for nonwoven products made from electrospun fibers are filtration materials, diaper covers, medical and personal hygiene products, thermal isolation products and clothes having predetermined characteristics, such as biological protection clothes and the like.

In a number of electrospinning applications, particularly in medical implementations, a combination of predetermined strength and elastic properties is required. For example, stent fiber coating should be capable both to expand diameter by hundreds of percents, without strength property degradation, and to preserve an ability for long-term service. Similar problems arise by designing vascular grafts, cardiac valves, and the like. The strength of the nonwoven polymer fiber web depends upon the orientation of the fibers, the mechanical characteristics of the polymer being used, the geometrical size and form of the fibers and the stretching extent of the fibers.

Heretofore, electrospinning has been efficiently used for generating various products. However, conventional nonwoven products exhibit less than optimal cross-directional strength, and less than optimal cross-directional strength in combination with high elongation. The nature of the conventional electrospinning process prevents efficient generation of products having optimal mechanical properties, in particular prior art electrospinning methods cannot be effectively used for manufacturing products having sufficient strength and elasticity.

There is thus a widely recognized need for, and it would be highly advantageous to have, a method of manufacturing a nonwoven material devoid of the above limitations.

SUMMARY OF THE INVENTION

According to one aspect of the present invention there is provided an apparatus for forming a nonwoven material from a liquefied polymer, the apparatus comprising: (a) a precipitation electrode; (b) a dispenser spaced apart from the precipitation electrode, defining a first axis therebetween, and being at a first potential relative to the precipitation electrode, the dispenser is constructed and designed for dispensing the liquefied polymer to provide a plurality of fibers; and (c) a mechanism for intertwining at least a portion of the plurality of polymer fibers so as to provide at least one polymer fiber bundle moving in a direction of the precipitation electrode, hence forming the nonwoven material thereupon.

According to further features in preferred embodiments of the invention described below, the mechanism for intertwining at least a portion of the plurality of polymer fibers comprises at least one blower constructed so as to twist the polymer fibers about the first axis.

According to still further features in the described preferred embodiments the mechanism for intertwining at least a portion of the plurality of polymer fibers comprises a motion mechanism connected to the dispenser, and operable to move of the dispenser about the first axis.

According to still further features in the described preferred embodiments the motion of the dispenser is selected from the group consisting of a circular motion, an ellipsoidal motion and a motion following an irregular pattern.

According to still further features in the described preferred embodiments the mechanism for intertwining at least a portion of the plurality of polymer fibers comprises a system of electrodes, being laterally displaced from the dispenser, being at a second potential relative to the precipitation electrode and capable of providing an electric field having at least one rotating component about the first axis According to another aspect of the present invention there is provided an apparatus for forming a nonwoven material from a liquefied polymer, the apparatus comprising: (a) a precipitation electrode; (b) a dispenser spaced apart from the precipitation electrode, and defining a first axis therebetween, the dispenser being at a first potential relative to the precipitation electrode; and (c) a system of electrodes being laterally displaced from the dispenser, being at a second potential relative to the precipitation electrode and capable of providing an electric field having at least one rotating component about the first axis; the dispenser and the system of electrodes being designed and constructed such that the liquefied polymer is dispensed from the dispenser and forms a plurality of entangled fibers moving in a direction of the precipitation electrode, hence forming the nonwoven material thereupon.

According to yet another aspect of the present invention there is provided a method of forming a liquefied polymer into a nonwoven material, the method comprising: (a) dispensing the liquefied polymer in a direction of a precipitation electrode, thereby providing a plurality of polymer fibers; (b) entangling at least a portion of the plurality of polymer fibers so as to provide at least one polymer fiber bundle; and (c) using the precipitation electrode to collect the at least one polymer fiber bundle thereupon, hence forming the nonwoven material.

According to still another aspect of the present invention there is provided an apparatus for forming a nonwoven material from a liquefied polymer, the apparatus comprising: (a) a precipitation electrode; (b) a dispenser spaced apart from the precipitation electrode, and defining a first axis therebetween, the dispenser being at a first potential relative to the precipitation electrode; and (c) at least one rotating electrode being laterally displaced from the dispenser, being at a second potential relative to the precipitation electrode and operable to rotate about the first axis; the dispenser and the at least one rotating electrode being designed and constructed such that the liquefied polymer is dispensed from the dispenser and forms a plurality of entangled fibers moving in a direction of the precipitation electrode, hence forming the nonwoven material thereupon.

According to an additional aspect of the present invention there is provided a method of manufacturing an apparatus for forming a nonwoven material from a liquefied polymer, the method comprising: (a) providing a precipitation electrode; (b) providing a dispenser, being at a first potential relative to the precipitation electrode; (c) positioning the dispenser, at a first distance from the precipitation electrode thereby defining a first axis therebetween; and (d) positioning at least one rotating electrode, being at a second potential relative to the precipitation electrode, laterally from the dispenser, the at least one rotating electrode operable to rotate about the first axis; the dispenser and the at least one rotating electrode are designed and constructed such that the liquefied polymer is dispensable from the dispenser to form a plurality of entangled fibers movable in a direction of the precipitation electrode, so as to form the nonwoven material thereupon.

According to further features in preferred embodiments of the invention described below, the method further comprising mixing the liquefied polymer with a charge control agent prior to the step of dispensing.

According to still further features in the described preferred embodiments the step of dispensing comprises dispensing the liquefied polymer from a dispenser, being at a first potential relative to the precipitation electrode.

According to still further features in the described preferred embodiments the step of entangling comprises providing an electric field having at least one rotating component around a first axis defined between the precipitation electrode and the dispenser.

According to still further features in the described preferred embodiments the step of providing an electric field having at least one rotating component, is done by providing at least one rotating electrode, being laterally displaced from the dispenser, being at a second potential relative to the precipitation electrode and operable to rotate about the first axis.

According to still further features in the described preferred embodiments the step of providing an electric field having at least one rotating component, is done by providing a system of electrodes, being laterally displaced from the dispenser, being at a second potential relative to the precipitation electrode and operable to provide a time-dependent electric field.

According to still further features in the described preferred embodiments the method further comprising reducing non-uniformities in the electric field.

According to still further features in the described preferred embodiments the step of reducing non-uniformities in the electric field is done by positioning a subsidiary electrode, being at a third potential relative to the precipitation electrode, close to the precipitation electrode.

According to still further features in the described preferred embodiments the method further comprising controlling fiber orientation of the nonwoven material formed upon the precipitation electrode.

According to still further features in the described preferred embodiments the step of controlling fiber orientation is done by positioning a subsidiary electrode, being at a third potential relative to the precipitation electrode, nearby to the precipitation electrode.

According to still further features in the described preferred embodiments the system of electrodes includes at least one rotating electrode, operable to rotate about the first axis.

According to still further features in the described preferred embodiments the precipitation electrode is operable to rotate around a second axis.

According to still further features in the described preferred embodiments the first axis and the second axis are substantially orthogonal.

According to still further features in the described preferred embodiments the first axis and the second axis are substantially parallel.

According to still further features in the described preferred embodiments the precipitation electrode is selected from the group consisting of a cylindrical precipitation electrode, a flat precipitation electrode and an intricate-profile precipitation electrode.

According to still further features in the described preferred embodiments the dispenser and the at least one rotating electrode are operable to synchronously move along the precipitation electrode.

According to still further features in the described preferred embodiments the dispenser and the at least one rotating electrode are operative to independently move along the precipitation electrode.

According to still further features in the described preferred embodiments the dispenser comprises a mechanism for forming a jet of the liquefied polymer.

According to still further features in the described preferred embodiments the mechanism for forming a jet of the liquefied polymer includes a dispensing electrode.

According to still further features in the described preferred embodiments the apparatus further comprising a bath for holding the liquefied polymer.

According to still further features in the described preferred embodiments the apparatus further comprising a subsidiary electrode being positioned close to the precipitation electrode and being at a third potential relative to the precipitation electrode, the subsidiary electrode being for modifying an electric field generated by the precipitation electrode, the dispenser and the system of electrodes.

According to still further features in the described preferred embodiments the subsidiary electrode serves for reducing non-uniformities in the electric field.

According to still further features in the described preferred embodiments the subsidiary electrode serves for controlling fiber orientation of the nonwoven material formed upon the precipitation electrode.

According to still further features in the described preferred embodiments the subsidiary electrode is of a shape selected from the group consisting of a plane, a cylinder, a torus and a wire.

According to still further features in the described preferred embodiments the subsidiary electrode is operative to move along the second axis.

According to still further features in the described preferred embodiments the subsidiary electrode is tilted at angle with respect to the second axis.

According to yet an additional aspect of the present invention there is provided a nonwoven material comprising at least one layer of bundles of intertwined fibers, the bundles being arranged in a predetermined orientation with respect to one another.

According to still an additional aspect of the present invention there is provided a tubular element comprising at least one layer of a nonwoven material which comprises bundles of intertwined fibers, the bundles being arranged in a predetermined orientation with respect to one another.

According to further features in preferred embodiments of the invention described below, the predetermined orientation is a random orientation.

According to still further features in the described preferred embodiments the fibers are polymer fibers.

According to still further features in the described preferred embodiments the polymer is a biocompatible polymer.

According to still further features in the described preferred embodiments the tubular element having at least one characteristic selected from the group consisting of: (a) having a diameter ranging from 0.01 mm to 100 mm; (b) capable of expanding by at least 150%; (c) having a porosity of at least 60%; (d) having pores, a diameter of which is ranging from 50 nm to 20 µm; and (e) having a predetermined permeability to liquid passing therethrough.

According to still further features in the described preferred embodiments the liquid is selected from the group consisting of blood, blood component, urine, fuel, oil and water.

The present invention successfully addresses the shortcomings of the presently known configurations by providing an electroejection apparatus and method capable of improving mechanical characteristics of nonwoven materials.

Implementation of the method and apparatus of the present invention involves performing or completing selected tasks or steps manually, automatically, or a combination thereof. Moreover, according to actual instrumentation and equipment of preferred embodiments of the method and apparatus of the present invention, several selected steps could be implemented by hardware or by software on any operating apparatus of any firmware or a combination thereof. For example, as hardware, selected steps of the invention could be implemented as a chip or a circuit. As software, selected steps of the invention could be implemented as a plurality of software instructions being executed by a computer using any suitable operating apparatus. In any case, selected steps of the method and apparatus of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of a method and an apparatus for forming a nonwoven material using electroejection. Specifically, the present invention can be used to manufacture nonwoven materials having improved mechanical properties via electroejection.

Figure 1:
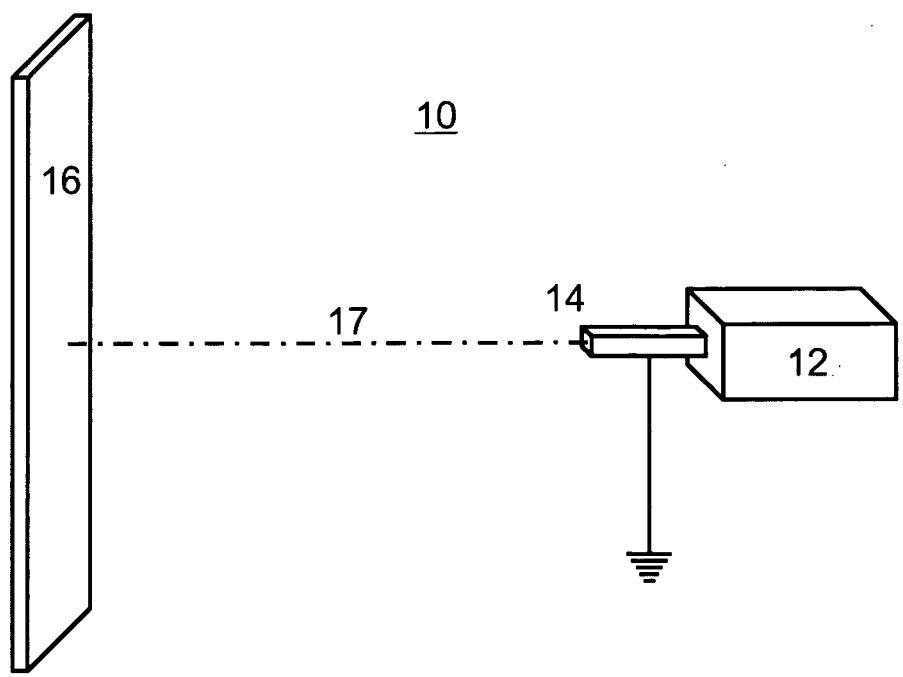
FIG. 1 is a schematic illustration of a prior art electrospinning apparatus.
Figure 2:
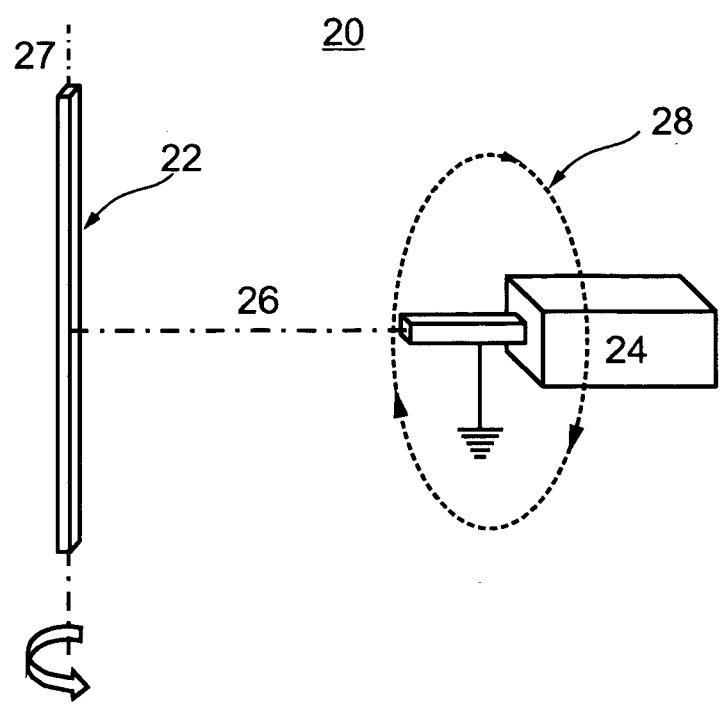
FIG. 2 is a schematic illustration of an electroejection apparatus according to the present invention.
Figure 3:
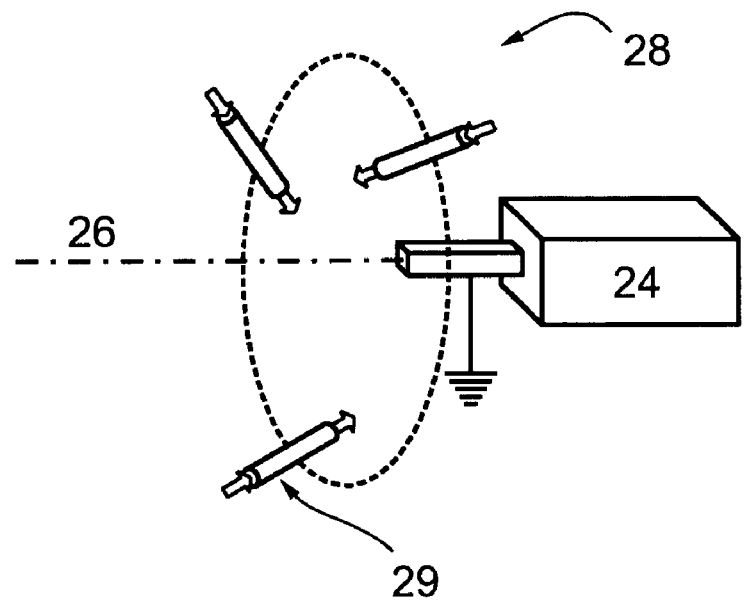
FIG. 3 is a schematic illustration of a mechanism for intertwining the polymer fibers manufactured as at least one blower, according to the present invention.
Figure 4:
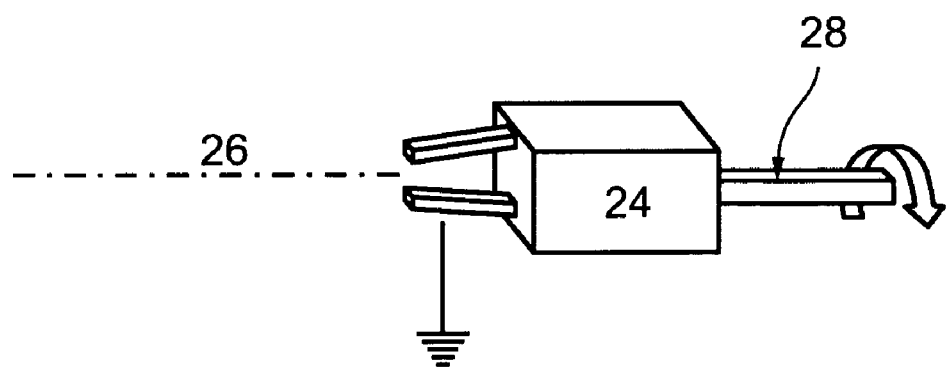
FIG. 4 is a schematic illustration of the mechanism for intertwining the polymer fibers in the form of motion mechanism connected to the dispenser, according to the present invention.

For purposes of better understanding the present invention, as illustrated in FIGS. 2–4 of the drawings, reference is first made to the construction and operation of a conventional (i.e., prior art) electrospinning apparatus as illustrated in FIG. 1.

FIG. 1 illustrates an apparatus for manufacturing a nonwoven material using a conventional electrospinning apparatus, which is referred to herein as apparatus 10.

Apparatus 10 includes a dispenser 12 which can be, for example, a bath provided with one or more capillary apertures 14. Dispenser 12 serves for storing the polymer to be spun in a liquid form, i.e., dissolved or melted. Dispenser 12 is positioned at a predetermined distance from a precipitation electrode 16, defining a first axis 17 therebetween. Precipitation electrode 16 serves for forming a structure thereupon. Precipitation electrode 16 is typically manufactured in accordance with the geometrical properties of the final product which is to be fabricated.

Dispenser 12 is typically grounded, while precipitation electrode 16 is connected to a source of high voltage, preferably of negative polarity, thus forming an electric field between dispenser 12 and precipitation electrode 16. Alternatively, precipitation electrode 16 can be grounded while dispenser 12 is connected to a source of high voltage with positive polarity.

To generate a nonwoven material, a liquefied polymer (e.g., melted polymer or dissolved polymer) is extruded, for example under the action of hydrostatic pressure, or using a pump (not shown in FIG. 1), through capillary apertures 14 of dispenser 12. As soon as meniscus of the extruded liquefied polymer forms, a process of solvent evaporation or cooling starts, which is accompanied by the creation of capsules with a semi-rigid envelope or crust. An electric field, occasionally accompanied by a unipolar corona discharge in the area of dispenser 12, is generated by the potential difference between dispenser 12 and precipitation electrode 16. Because the liquefied polymer possesses a certain degree of electrical conductivity, the above-described capsules become charged. Electric forces of repulsion within the capsules lead to a drastic increase in hydrostatic pressure. The semi-rigid envelopes are stretched, and a number of point micro-ruptures are formed on the surface of each envelope leading to spraying of ultra-thin jets of liquefied polymer from dispenser 12.

Under the effect of a Coulomb force, the jets depart from dispenser 12 and travel towards the opposite polarity electrode, i.e., precipitation electrode 16. Moving with high velocity in the inter-electrode space, the jet cools or solvent therein evaporates, thus forming fibers which are collected on the surface of precipitation electrode 16.

In a typical electrospinning process (e.g., as employed by apparatus 10), the electric field, generated between dispenser 12 and precipitation electrode 16, is static and the field lines are in general substantially parallel in the inter-electrode space. Hence, the charged polymer fibers, which tend to align with the field lines, move along non-intersecting trajectories, and contact with each other only on precipitation electrode 16. The effect is aggravated by mutual electrostatic repulsion forces between the fibers, preventing the fibers to entangle with each other while moving in the inter-electrode space.

The strength of the formed nonwoven material depends on the mechanical characteristics of the polymer used in the electrospinning process, such as a modulus of elasticity and rupture strength, as well as on the geometrical properties of the polymer fibers, such as their cross-sectional areas and shapes. Thus, for example, a single thick fiber is known to have more strength than a single thin fiber.

However, it is known that the strength of a plurality of thin fibers grouped into a bundle is significantly higher than that of a single fiber, even for a fiber having diameter which is larger than the diameter of the bundle. Moreover, the strength such bundle is significantly higher than that of a plurality of fibers which are not grouped into a bundle (for example if the fibers are oriented substantially parallel to each other, without any physical contact between fibers). The enhancement of the strength is explained by a uniform distribution of the load on the bundle due to friction forces, the amount of which is increasing with the number and extent of intersect points between the fibers in the bundle. In other words the larger is the total surface contact between the fibers in the bundle—the larger is the strength of the bundle.

In the field of nonwoven materials and in particular in nonwoven materials fabricated using electrospinning, there are continuing challenges to enhance the strength of the final products, while maintaining other advantageous features, such as, low basis weight, relatively small thickness, porosity, biocompatibility, filtering capabilities and the like. Additional important feature in many applications is elongation ability of the final product. It should be appreciated that the strength of nonwoven materials fabricated using prior art electrospinning devices, e.g., apparatus 10, is dictated by the polymeric material and by the thickness and shape of the fibers. These parameters are typically chosen in accordance with the desired features of the final product, and often compromises are made with respect to one or more parameters.

While reducing the present invention to practice, it was unexpectedly uncovered that the strength of the nonwoven material may be significantly enhanced, by providing an electrospinning apparatus employing a rotating electric field, which is referred to hereinbelow as electroejection apparatus 20.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now again to the drawings, FIG. 2 illustrates apparatus 20 for forming a nonwoven material from a liquefied polymer. Apparatus 20 includes a precipitation electrode 22 and a dispenser 24 which is spaced apart from precipitation electrode 22, and defining a first axis 26 therebetween. Dispenser 24 is preferably at a first potential relative to precipitation electrode 22. According to a preferred embodiment of the present invention, dispenser 24 may be operable to move along precipitation electrode 22, so as to ensure complete or predetermined covering of precipitation electrode 22, as is further described hereinunder. In addition, precipitation electrode 22 may be operable to rotate around a second axis 27 having any angle relative to first axis 26. Thus, for example, second axis 27 and first axis 26 may be substantially orthogonal or substantially parallel.

Apparatus 20 further includes a mechanism 28 for intertwining at least a portion of the polymer fibers, so as to provide at least one polymer fiber bundle moving in a direction of precipitation electrode 22, hence forming the nonwoven material thereupon. Mechanism 28 may include any mechanical and/or electronical components which are capable for intertwining the polymer fibers "on the fly", as is further detailed hereinunder, with reference to FIGS. 3–5.

Thus, FIG. 3 illustrates one embodiment of the present invention in which mechanism 28 is realized as at least one blower 29, constructed so as to twist the polymer fibers around first axis 26. Blower 29 is designed and constructed, such that an air flow is provided in the inter electrode space, which air flow is characterized by sufficient turbulence capable of entangling the fibers dispensed by dispenser 24. As air flow is known to have a decaying property, the number, shape and orientation of the blowers should be chosen such that the polymer fibers are affected by the turbulence over the entire motion in the inter electrode space.

FIG. 4 illustrates another embodiment of the present invention in which mechanism 28 is realized as a motion mechanism connected to dispenser 24 and operable to move dispenser 24 about the first axis. According to a preferred embodiment of the present invention, the motion of dispenser 24 may be a circular motion, an ellipsoidal motion or any motion following an irregular pattern, provided that such motion entangles the polymer fibers dispensed by dispenser 24. It would be appreciated that a pronounced effect of such motion can be achieved by a motion having a non-zero tangential acceleration. This ensures that different fibers move with different motion characteristics and eventually entangle one with the other.

Figure 5:
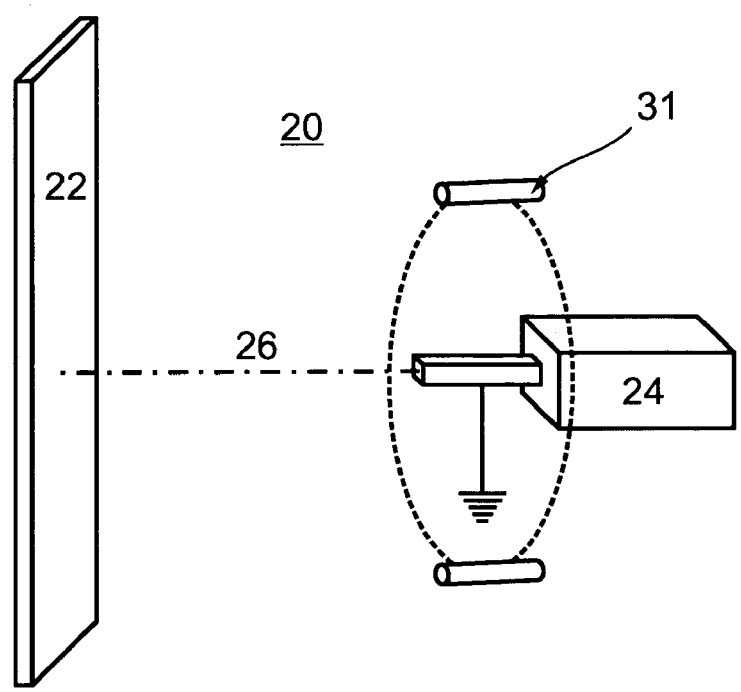
FIG. 5 is a schematic illustration of an electroejection apparatus in which the mechanism for intertwining the polymer fibers is a system of electrodes, according to the present invention.

Reference is now made to FIG. 5, illustrating a third embodiment of the invention in which mechanism 28 includes a system of electrodes 31 being laterally displaced from dispenser 24 and preferably at a second potential relative to precipitation electrode 22. According to a preferred embodiment of the present invention system of electrodes 31 may be constructed in any way known in the art for providing an electric field rotating around first axis 26.

Figure 6:
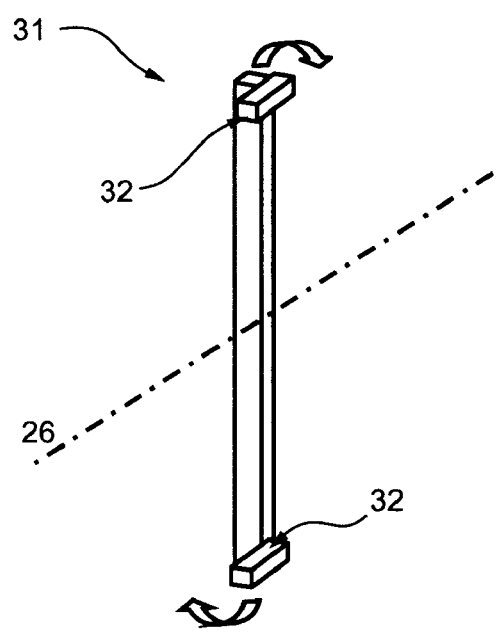
FIG. 6 is a schematic illustration of a rotating electrode according to the present invention.

Reference is now made to FIG. 6, in which system of electrodes 31 is manufactured as at least one rotating electrode 32, operable to rotate around first axis 26. Rotating electrode 32, being at a second potential relative to precipitation electrode 22 (not shown in FIG. 6), generates an electric field, the direction of which follows the motion of rotating electrode 32, hence an electric field having at least one rotating component is generated.

Figure 7:
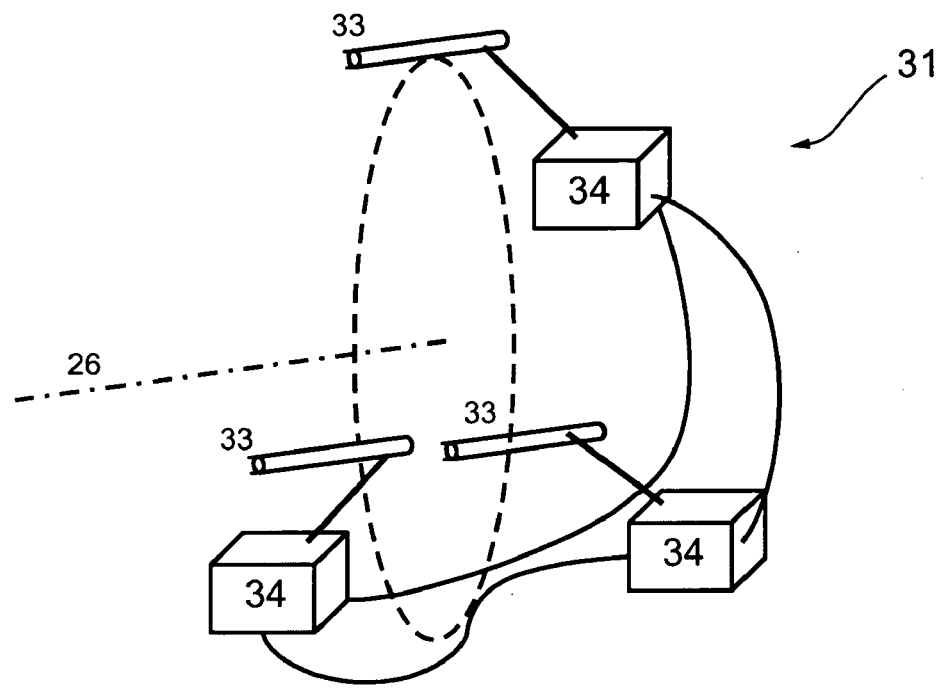
FIG. 7 is a schematic illustration of a system of stationary electrodes according to the present invention.

Reference is now made to FIG. 7, which depicts system of electrodes 31 according to another preferred embodiment of the present invention. Thus, system of electrodes 31 may include two or more stationary electrodes 33, connected to at least one power source 34, so that the potential difference between system of electrodes 31 and precipitation electrode 22 (and between system of electrodes 31 and dispenser 24) varies in time. Power sources 34, being electronically communicating with each other so as to synchronize a relative phase between electrodes 33. Hence, each of stationary electrodes 33 generates a time-dependent electric field having a constant direction. The electronic communication between power sources 34 ensures that the sum of all (time-dependent) field vectors is rotating around first axis 26.

According to a preferred embodiment of the present invention, in order to ensure that the rotating field will affect different locations of the inter-electrode space, system of electrodes 31 may be operable to move along precipitation electrode 22. It will be appreciated that in the preferred embodiment in which both dispenser 24 and system of electrodes 31 are capable of such longitudinal motion, such motion may be either independent or synchronized.

In operation mode of apparatus 20, the liquefied polymer is dispensed by dispenser 24, and then, subjected to the electric field, moves in the inter-electrode space. The electric field in the inter-electrode space has at least one rotating component around first axis 26 (generated by the potential difference between system of electrodes 31 and precipitation electrode 22) and a stationary electric field (generated by the potential difference between dispenser 24 and precipitation electrode 22). Hence, in addition to the movement in the direction of precipitation electrode 22, the jets of liquefied polymer, under the effect of the rotating component of the electric field twist around first axis 26. The rotation frequency may be controlled by a suitable choice of configuration for system of electrodes 31, as well as on the value of the potential differences employed.

At a given time, the effect of the rotating component of the electric field on the jets neighboring system of electrodes 31 is larger than the effect on the jets which are located far from system of electrodes 31. Hence, the trajectories of the fibers start crossing one another, resulting in physical contacts and entanglement between fibers prior to precipitation.

Thus, apparatus 20 generates higher-order formations of fiber bundles from the elementary fibers in the spray jet. The structure of the formed fiber bundles is inhomogeneous and depends on the distance of the fiber bundle from system of electrodes 31. Specifically, the extent of fiber twisting and interweaving, and the amount of fibers in the bundle, is an increasing function of the distance from system of electrodes 31. During the motion of the bundles in the inter-electrode space, they may also intertwine with one another, forming yet thicker bundles. A typical diameter of the fiber bundles is ranging from 0.5 μm to 15 μm, which diameter depends on the chemical nature of the polymer used.

The bundles, while formed, continue to move in the inter-electrode space, directed to precipitation electrode 22, forming the nonwoven material thereupon. The formed material has three-dimensional reticular structure, characterized by a large number of sliding contacts between fibers. As explained above, such contacts significantly increase the strength of the material, due to friction forces between fibers. The ability of fibers for mutual displacement increases the elasticity of the nonwoven material under loading, according to a preferred embodiment of the present invention, the formed material is capable of expanding by at least 150%. Another unique feature of bundle based nonwoven material, is that the obtained porosity is characterized by both large and small pores. The large pores, typically of 10 μm in diameter, being generated by the intertwining of relatively thick bundles, whereas the small pores, typically of 0.1 μm in diameter, are formed within the bundles. A typical situation is that the number of large pores is larger than the number of small pores. The mean pore size ensures that the nonwoven material manufactured in accordance with the preferred embodiments of the present invention, may be used as a filter, having enhanced mechanical characteristics, or as a carrier to a filter.

According to a preferred embodiment of the present invention, precipitation electrode 22 may have different shapes depending on the desired structure of the fabricated nonwoven material. For example, precipitation electrode 22 may be manufactured as a cylinder, a plane (i.e., a flat precipitation electrode) or it may even have an intricate-profile.

The electroejection apparatus described hereinabove can be efficiently used for generating nonwoven materials upon a precipitation electrode having or large radius of curvature, e.g., a flat precipitation electrode (which may be considered as having an infinite radius of curvature) or a large diameter tubular precipitation electrode. However, when using a precipitation electrode being at least partially with small radius of curvature, the orientation of the electric field maximal strength vector is such that precipitation electrode 22 is coated coaxially by the bundles. Thus, small diameter products, may exhibit limited radial strength.

In cases where precipitation electrode 22 comprises sharp edges and/or variously shaped and sized recesses, the electric field magnitude in the vicinity of precipitation electrode 22 may exceed the air electric strength (about 30 kV/cm), and a corona discharge may develop in the area of precipitation electrode 22. The effect of corona discharge decreases the coating efficiency of the process as further detailed herein.

Corona discharge initiation is accompanied by the generation of a considerable amount of air ions having opposite charge sign with respect to the charged fibers. Since an electric force is directed with respect to the polarity of charges on which it acts, theses ions start to move at the opposite direction to fibers motion i.e., from precipitation electrode 22 towards dispenser 24. Consequently, a portion of these ions generate a volume charge (ion cloud), non-uniformly distributed in the inter-electrode space, thereby causing electric field lines to partially close on the volume charge rather than on precipitation electrode 22. Moreover, the existence of an opposite volume charges in the inter-electrode space, decreases the electric force on the fibers, thus resulting in a large amount of fibers accumulating in the inter-electrode space. Such an effect may lead to a low-efficiency process of fiber coating, and may even result in a total inability of fiber-bundles to be collected upon precipitation electrode 22.

The present invention successfully addresses both of the above problems, by providing a subsidiary electrode within apparatus 20, so as to control both the stationary and the rotating components of the electric field. Specifically, a subsidiary electrode may either substantially decreases non-uniformities in the electric field components and/or provides for controlled bundles orientation upon deposition.

Figure 8:
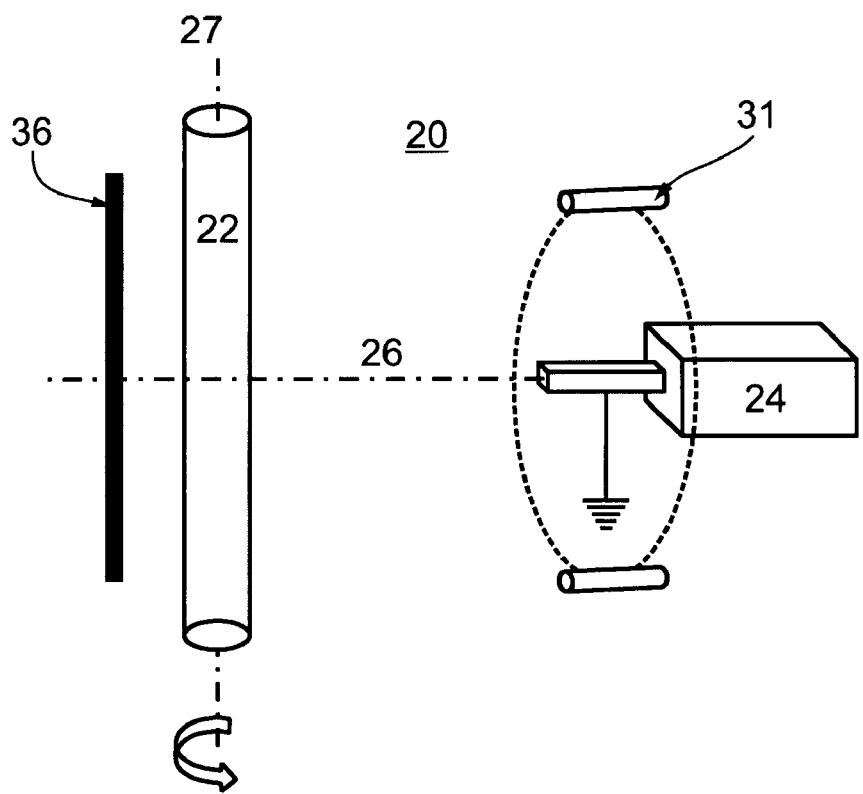
FIG. 8 is a schematic illustration of an electroejection apparatus, further comprising a subsidiary electrode, according to the present invention.

Reference is now made to FIG. 8, which depicts another preferred embodiment of the present invention, which may be employed for fabricating nonwoven shells having a small diameter and/or intricate-profile. Hence, apparatus 20 may further comprise a subsidiary electrode 36 which is kept at a third potential difference relative to precipitation electrode 22. Subsidiary electrode 36 serves for controlling the direction and magnitude of the electric field in the inter-electrode space and as such, subsidiary electrode 36 can be used to control the orientation of polymer fiber bundles deposited on precipitation electrode 22. In some embodiments, subsidiary electrode 36 serves as a supplementary screening electrode. Broadly stated, use of screening results in decreasing the coating precipitation factor, which is particularly important upon precipitation electrodes having at least a section of small radii of curvature. According to a preferred embodiment of the present invention the size, shape, position and number of subsidiary electrode 36 is selected so as to maximize the coating precipitation factor, while minimizing the effect of corona discharge in the area of precipitation electrode 22 and/or so as to provide for controlled fiber bundles orientation upon deposition. Thus, subsidiary electrode 36 may be fabricated in a variety of shapes each serving a specific purpose. Electrode shapes which can be used with apparatus 20 of the present invention include, but are not limited to, a plane, a cylinder, a torus a rod, a knife, an arc or a ring.

According to a presently preferred embodiment of the invention, subsidiary electrode 36 may be operable to move along second axis 27. Such motion may be in use when enhanced control over fiber orientation is required. The longitudinal motion of subsidiary electrode 36 may be either independent or synchronized with any of the other longitudinal motions of dispenser 24 and of system of electrodes 31. Subsidiary electrode 36 may also be tilted through an angle of 45°–90° with respect to second axis 27, which tilting may be used to provide for controlled fiber-bundle orientation upon deposition, specifically, large angles result in predominant polar (transverse) orientation of bundles.

The electroejection process described hereinabove, ensures efficient manufacturing of tubular elements, which enjoy several mechanical and physical characteristics.

Hence, according to a preferred embodiment of the present invention, there is provided a tubular element comprising at least one layer of a nonwoven material which comprises bundles of intertwined fibers. The bundles being arranged in a predetermined orientation with respect to one another, which may be a random orientation, an axial orientation, a transverse (polar) orientation or any other orientation with respect to the longitudinal axis of the tubular element. The tubular element having various of physical and mechanical properties, which may be any combination of the following characteristics: (a) having a diameter ranging from 0.01 mm to 100 mm; (b) capable of expanding by at least 150%; (c) having a porosity of at least 60%; (d) having pores, a diameter of which is ranging from 50 nm to 20 µm; and (e) having a predetermined permeability to liquid passing therethrough.

The tubular element may be used for various applications in the industry, specifically as a synthetic blood vessel or as any liquid/gas tube. It may also serve as a container or bladder in applications in which such geometry is required. Hence the tubular element is capable of preventing leakage of e.g. blood, urine, fuel, oil and water flowing therethrough.

According to a preferred embodiment of the present invention, the liquefied polymer loaded into dispenser 24 may be, for example polyurethane, polyester, polyolefin, polymethyl methacrylate, polyvinyl aromatic, polyvinyl ester, polyamide, polyimide, polyether, polycarbonate, polyacrilonitrile, polyvinyl pyrrolidone, polyethylene oxide, poly (L-lactic acid), poly (lactide-CD-glycoside), polycaprolactone, polyphosphate ester, poly (glycolic acid), poly (DL-lactic acid), and some copolymers. Biolmolecules such as DNA, silk, chitozan and cellulose may also be used. Improved charging of the polymer may also be required. Improved charging is effected according to the present invention by mixing the liquefied polymer with a charge control agent (e.g., a dipolar additive) to form, for example, a polymer-dipolar additive complex which apparently better interacts with ionized air molecules formed under the influence of the electric field. The charge control agent is typically added in the grams equivalent per liter range, say, in the range of from about 0.001 N to about 0.1 N, depending on the respective molecular weights of the polymer and the charge control agent used.

U.S. Pat. Nos. 5,726,107; 5,554,722; and 5,558,809 teach the use of charge control agents in combination with polycondensation processes in the production of electret fibers, which are fibers characterized in a permanent electric charge, using melt spinning and other processes devoid of the use of a precipitation electrode. A charge control agent is added in such a way that it is incorporated into the melted or partially melted fibers and remains incorporated therein to provide the fibers with electrostatic charge which is not dissipating for prolonged time periods, say weeks or months. In a preferred embodiment of the present invention, the charge control agent transiently binds to the outer surface of the fibers and therefore the charge dissipates shortly thereafter. This is because polycondensation is not exercised at all such that the chemical interaction between the agent and the polymer is absent, and further due to the low concentration of charge control agent employed. The resulting nonwoven material is therefore, if so desired, substantially charge free.

Suitable charge control agents include, but are not limited to, mono- and poly-cyclic radicals that can bind to the polymer molecule via, for example, —C=C—, =C—SH— or —CO—NH— groups, including biscationic amides, phenol and uryl sulfide derivatives, metal complex compounds, triphenylmethanes, dimethylmidazole and ethoxytrimethylsians.

Additional objects, advantages, and novel features of the present invention will become apparent to one ordinarily skilled in the art upon examination of the following example, which is not intended to be limiting. Additionally, each of the various embodiments and aspects of the present invention as delineated hereinabove and as claimed in the claims section below finds experimental support in the following example.

EXAMPLE

Reference is now made to the following example, which together with the above descriptions, illustrate the invention in a non limiting fashion.

Vascular prostheses, 6 mm in diameter and 200 mm in length were manufactured. A rod, 6 mm in diameter and 300 mm in length was used as a precipitation electrode, and its central 200 mm portion was coated at ambient temperature (24° C.). The precipitation electrode was rotated at an angular velocity of 100 RPM.

A silicon polycarbonate urethane copolymer CarboSil 20 was purchased from Polymer Technology Group Incorporated, and was used for prostheses manufacturing. This polymer has satisfactory fiber-generation abilities, it is biocompatible and rather strong. A mixture of dimethylformamide and toluene of ratio ranging from 1:1 to 1:2 was used as a solvent in all experiments.

A spinneret was used as the dispensing electrode, the inner diameter of the spinneret was 0.5 mm, and the flow-rate was 3 ml/h. The dispensing electrode was grounded while the precipitation electrode was kept at a potential of −50 kV, relative to the dispensing electrode.

The dispensing electrode was positioned 35 cm from the precipitation electrode. Reciprocal motion of the dispensing electrode was enabled along the mandrel longitudinal axis at a frequency of 5 motions per minute.

A system of two rotating electrodes was used as a mechanism for intertwining the polymer fibers. The rotating electrodes, manufactured as metallic rods, where positioned 70 mm apart and perpendicular to a common base. The spinneret was located on the base, equidistant between the two electrodes, which spinneret was the center of the rotating system. The two metallic rods were 2–5 mm higher than the spinneret.

The grafts were manufactured using three alternative methods: (a) using conventional electrospinning, (b) using electroejection, employing a rotating electric field having a frequency of 100 $min^{-1}$ and (c) using electroejection, employing a rotating electric field having a frequency of 850 $min^{-1}$. The rotating electric field was employed using a rotating electrode, which was kept under a zero potential.

For comparison, all the parameters of the conventional electrospinning and of the electroejection were identical, except for the rotating electric field, which is a unique feature of the electroejection method.

The manufactured grafts were subjected to strength (longitudinal and radial) tests, water permeability tests, elongation tests and burst strength tests. In addition, the porosity of the grafts was measured in accordance to ANSI/AAMI VP20-1994.

Table 1 lists some comparative characteristics of the prostheses produced by a conventional electrospinning technique (i.e. using a static electric field) and by electroejection in a rotating electric field.

TABLE 1

| | Property | Static field | Rotating field 100 $min^{-1}$ | Rotating field 850 $min^{-1}$ |
|---|---|---|---|---|
| 1 | Graft longitudinal tensile strength, N | 42 | 45 | 54 |
| 2 | Graft radial tensile strength, N/25 mm | 78 | 84 | 92 |
| 3 | Water permeability, $cm^3/cm^2/min$ | 3.0 | 4.8 | 8.5 |
| 4 | Porosity, % | 72 | 74 | 80 |
| 5 | Linear density, gr/m | 6.0 | 6.0 | 6.0 |
| 6 | Graft ultimate elongation, % | 130 | 145 | 168 |
| 7 | Burst Strength | Passed | Passed | Passed |

As can be seen from Table 1, the rotating field, employed in accordance with the teachings of the present invention significantly increases the graft longitudinal and radial tensile strength. The water permeability and the porosity of the graft fabricated using conventional electrospinning are smaller comparable to the water permeability and porosity of the graft fabricated using the teaching of the present invention. In addition, the elongation ability of the graft is enhanced once the rotating field is employed.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An apparatus for forming a nonwoven material from a liquefied polymer, the apparatus comprising:

(a) a precipitation electrode;

(b) a dispenser spaced apart from said precipitation electrode, and defining a first axis therebetween, said dispenser being at a first potential relative to said precipitation electrode; and (c) at least one rotating electrode being laterally displaced from said dispenser, being at a second potential relative to said precipitation electrode and operable to rotate around said first axis;

said dispenser and said at least one rotating electrode being designed and constructed such that the liquefied polymer is dispensed from said dispenser and forms a plurality of entangled fibers moving in a direction of said precipitation electrode, hence forming the nonwoven material thereupon.

2. The apparatus of claim 1, wherein said precipitation electrode is operable to rotate around a second axis.

3. The apparatus of claim 2, wherein said first axis and said second axis are substantially orthogonal.

4. The apparatus of claim 2, wherein said first axis and said second axis are substantially parallel.

5. The apparatus of claim 1, wherein said precipitation electrode is selected from the group consisting of a cylindrical precipitation electrode and a flat precipitation electrode.

6. The apparatus of claim 1, herein said dispenser and said at least one rotating electrode are operable to synchronously move along said precipitation electrode.

7. The apparatus of claim 1, wherein said dispenser and said at least one rotating electrode are operative to independently move along said precipitation electrode.

8. The apparatus of claim 1, wherein said dispenser comprises a mechanism for forming a jet of the liquefied polymer.

9. The apparatus according to claim 8, wherein said mechanism for forming a jet of the liquefied polymer includes a dispensing electrode.

10. The apparatus according to claim 1, further comprising a bath for holding the liquefied polymer.

11. The apparatus of claim 2, further comprising a subsidiary electrode being positioned close to said precipitation electrode and being at a third potential relative to said precipitation electrode, said subsidiary electrode being for modifying an electric field generated by said precipitation electrode, said dispenser and said at least one rotating electrode.

12. The apparatus of claim 11, wherein said subsidiary electrode is designed and constructed such as to reduce non-uniformities in said electric field.

13. The apparatus of claim 11, wherein said subsidiary electrode is designed and constructed such as to control fiber orientation of the nonwoven material formed upon said precipitation electrode.

14. The apparatus of claim 11, wherein said subsidiary electrode is of a shape selected from the group consisting of a plane, a cylinder, a torus and a wire.

15. The apparatus of claim 11, wherein said subsidiary electrode is operative to move along said second axis.

16. The apparatus according to claim 11, wherein said subsidiary electrode is tilted at an angle with respect to said second axis.

* * * * *